United States Patent [19]

Tindall et al.

[11] Patent Number: 5,328,982
[45] Date of Patent: Jul. 12, 1994

[54] DEPOLYMERIZATION OF SUBSTANTIALLY AMORPHOUS POLYESTERS

[75] Inventors: George W. Tindall, Kingsport; Randall L. Perry, Bluff City; Art T. Spaugh, Jr., Kingsport, all of Tenn.

[73] Assignee: Eastman Chemical Company, Kingsport, Tenn.

[21] Appl. No.: 970,220

[22] Filed: Nov. 2, 1992

[51] Int. Cl.$^5$ ............................................. C08J 3/00
[52] U.S. Cl. .................................. 528/488; 528/481; 528/489; 528/493; 528/497; 528/503; 134/29; 562/483; 562/485; 560/78; 560/79
[58] Field of Search ............... 528/481, 488, 489, 493, 528/497, 503; 134/29; 562/483, 485; 560/78, 79

[56] References Cited

U.S. PATENT DOCUMENTS

| | | | |
|---|---|---|---|
| 3,120,561 | 2/1964 | Chambret | 562/483 |
| 3,952,053 | 4/1976 | Brown, Jr. et al. | 562/483 |
| 4,078,143 | 3/1978 | Malik et al. | 560/78 |
| 4,163,860 | 8/1979 | Delattre et al. | 560/96 |
| 4,355,175 | 10/1982 | Puszkaszeri | 562/483 |
| 4,542,239 | 9/1985 | Lamparter et al. | 562/487 |
| 4,578,502 | 3/1986 | Cudmore | 560/79 |
| 4,605,762 | 8/1986 | Mandoki | 562/483 |
| 4,620,032 | 10/1986 | Doerr | 562/483 |
| 4,876,378 | 10/1989 | VanSickle | 560/78 |
| 5,045,122 | 9/1991 | Tindall et al. | 134/29 |

FOREIGN PATENT DOCUMENTS 453369 1/1965 Japan.

OTHER PUBLICATIONS

*Anal. Chem.* 34 (1962) 1173 G. G. Esposito.
*Anal. Chem.* 37 (1965) 1709 J. Jankowski & P. Garner.
*Anal. Chem.* 37 (1965) 1306, J. R. Kirby, A. J. Baldwin and R. H. Heidner.
*Anal. Chem.* 264 (1973) 293, D. Vink, R. van Wijk.
*J. Appl. Poly. Sci.* 18 (1974) 1953 D. Nissen, V. Rossbach, and H. Zahn.
*Anal. Chem.* 34 (1962) 1048 G. G. Esposito and M. H. Swann.
*Makromol Chem.* 77 (1964) 153 R. Janssen, H. Ruysschaert, and R. Vroom.
*J. Oil Col. Chem. Assoc.* 50 (1967) 373 J. Rawlinson and E. L. Deeley.
*J. Chromatogr.* 351 (1986) 203 P. Perlstein and P. Orme.
*Anal. Chem.* 47 (1975) 1708 J. C. West.
*Anal. Chem.* 40 (1968) 229 L. H. Ponder.
*Anal. Chem.* 49 (1977) 741 B. J. Allen, G. M. Elsea, K. P. Keller and H. D. Kinder.
*J. Am. Chem. Soc.* 83 (1961) 117 J. Miller and A. J. Parker.
*Talanta* 13 (1966) 1673 J. A. Vinson, J. S. Fritz and C. A. Kingsbury.
*Physical Organic Chemistry*, Longmin Scientific and Technical, Longman Group UK Limited, Essex, England, N. Issacs.

*Primary Examiner*—Samuel A. Acquah
*Attorney, Agent, or Firm*—Mark A. Montgomery

[57] ABSTRACT

Ester bonds are hydrolyzed in the conversion of substantially amorphous polyesters to their monomeric components, by being contacted with a mixture of (a) an alcohol, such as methanol, or glycol, (b) a polar aprotic solvent such as N-methyl-pyrrolidone or dimethyl sulfoxide and (c) an alkoxide or hydroxide such as sodium hydroxide.

16 Claims, 2 Drawing Sheets

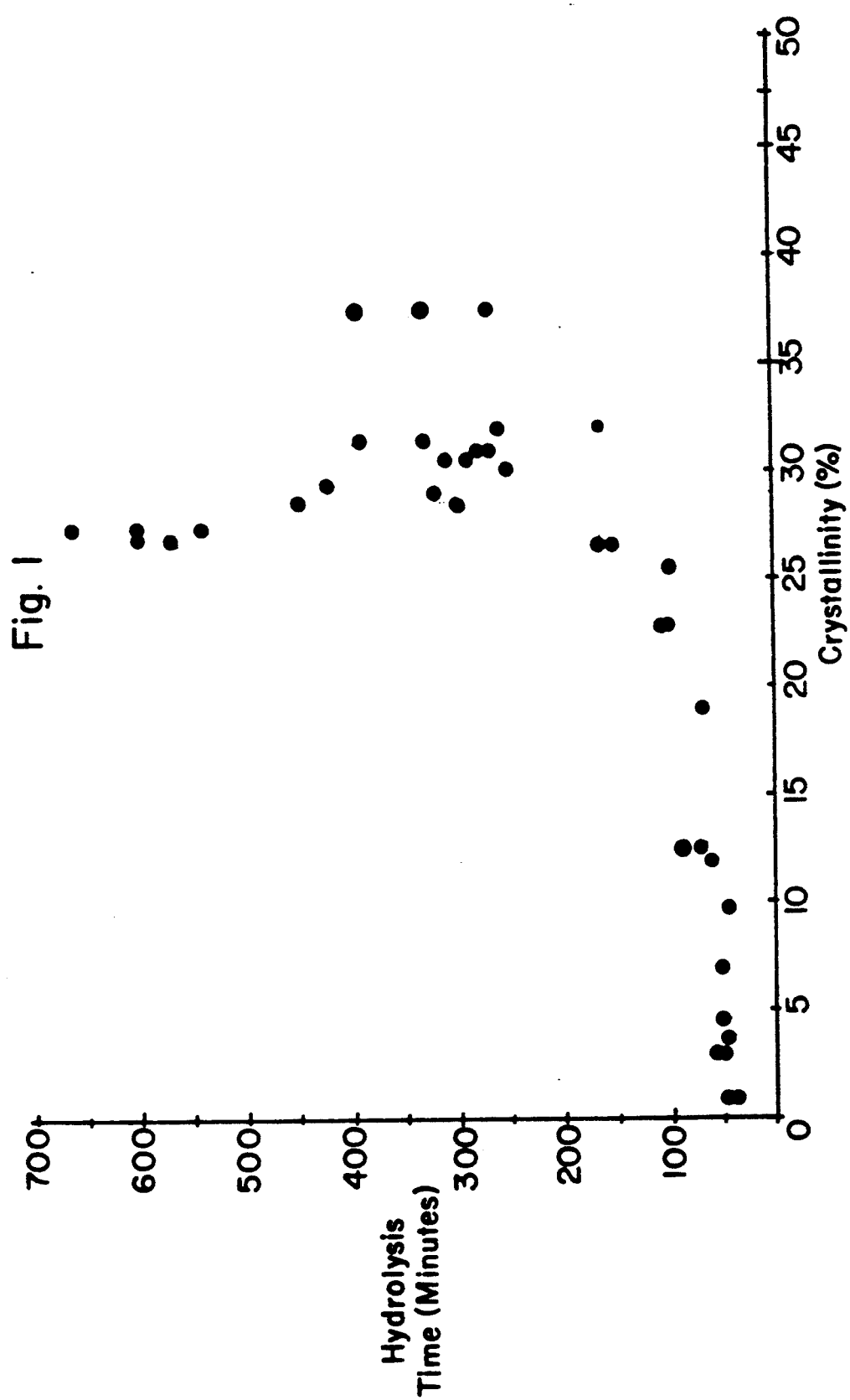

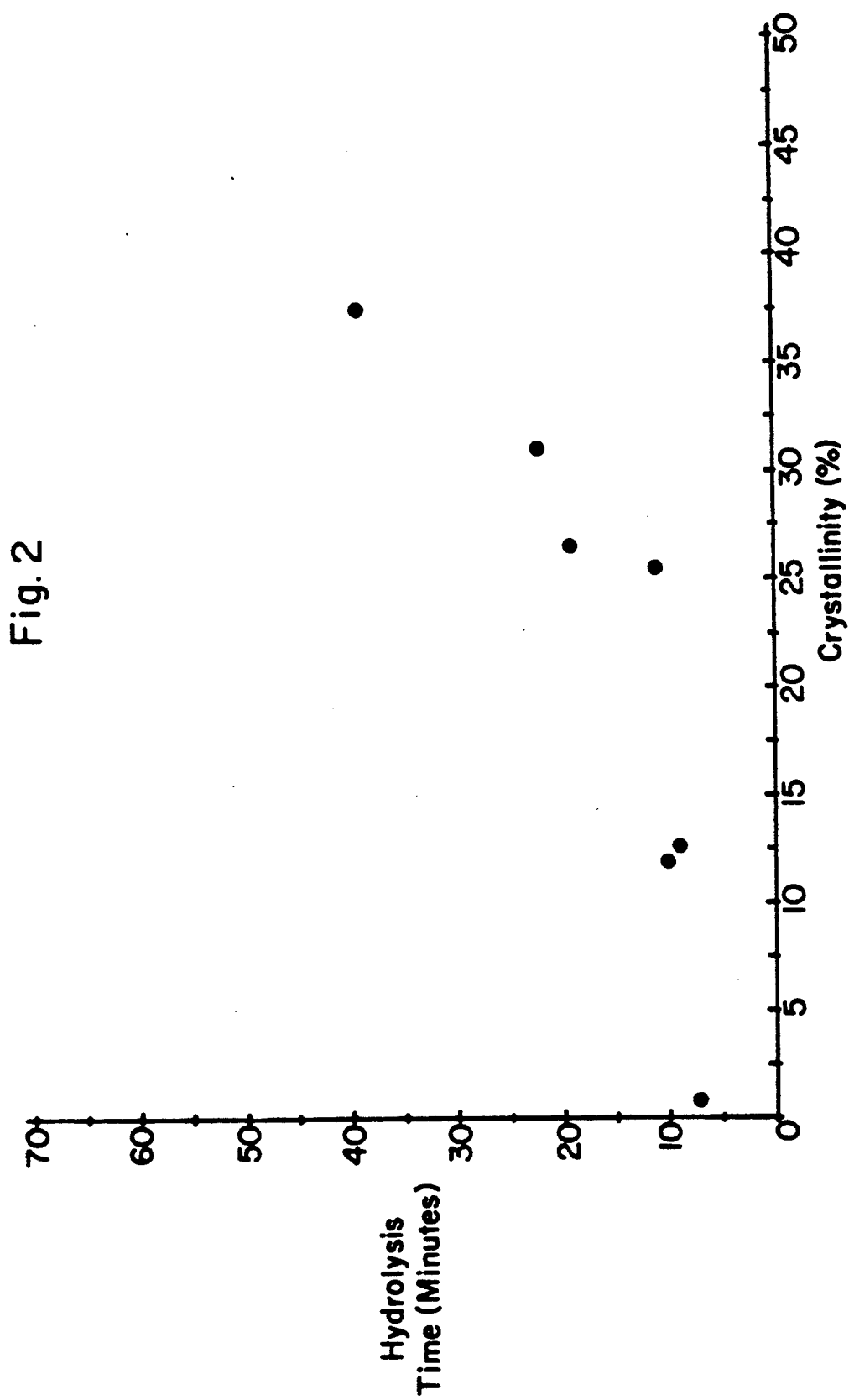

DEPOLYMERIZATION OF SUBSTANTIALLY AMORPHOUS POLYESTERS

FIELD OF THE INVENTION

The present invention relates to the recovery of monomeric components from polyesters by a hydrolysis process. More particularly the present invention relates to the hydrolysis of amorphous polyesters.

BACKGROUND OF THE INVENTION

The conversion of acids and alcohols to esters is well known, as is the conversion of esters to acids and alcohols. The conversion of many esters to acids and alcohols can be carried out by boiling the ester in a mixture of base and alcohol. However, the conversion of polyesters to their corresponding monomeric acids and glycols is very difficult. Polyesters are normally not soluble in the solvents that are used for the conversion of esters to alcohol and acid. Also, polyesters are often highly crystallized, further limiting their solubility and hindering the attack of the ester bonds by a base.

Methods are known for the conversion of some polyesters to their monomeric components. These depolymerization methods are generally used to recover monomers from polymer scrap for the repolymerization of the monomers, but can also be used to analyze the polymers to determine their monomer content.

Polyesters can be converted or depolymerized to amides and glycols by a process known as aminolysis. This process entails the refluxing of a polyester with a primary amine or hydrazine such as disclosed in ASTM Method D 2456 and, Anal. Chem. 34 (1962)1173 G. G. Esposito. However, the aminolysis process is generally slow and produces undesirable side reactions with some polyesters.

The transesterification of polyesters is another method of depolymerizing polymers. This method entails heating a polyester in excess alcohol or glycol, optionally in the presence of a catalyst such as disclosed in ASTM Method D 2455 and in Anal. Chem. 37 (1965)1709 J. Jankowski and P. Garner. The transesterification process, however, is generally very slow and high temperatures and pressures are needed to achieve practical conversion rates.

Another method of depolymerizing polyesters is by hydrolysis. This process entails the heating of a polyester with a base in the presence of a solvent, such as an alcohol, such as disclosed in Anal. Chem. 37 (1965)1306, J. R. Kirby, A. J. Baldwin, and R. H. Heidner; U.S. 4,605,762, and U.S. 4,620,032. Hydrolysis, however, is also generally slow at mild conditions, thus, requiring high temperatures and pressures to achieve rapid conversions.

In spite of the many known depolymerization processes, polyesters are not easily depolymerizable by any known process at ambient conditions.

In light of the above, it would, therefore, be very desirable to rapidly convert polyesters under relatively mild conditions of temperature and pressure without generating undesirable side reactions.

SUMMARY OF THE INVENTION

The process of the present invention rapidly depolymerizes substantially amorphous polyesters under relatively mild conditions without generating undesirable side reactions by using a composition comprising a mixture of (a) alcohol or glycol, (b) polar aprotic solvent, and (c) alkoxide or hydroxide. The alkoxide or hydroxide, the alcohol or glycol, and the polar aprotic solvent should be compatible so that the alkoxide or hydroxide will substantially dissolve at relatively high concentrations in the solvent mixture.

BRIEF DESCRIPTION OF DRAWINGS

FIG. 1 shows the hydrolysis times, at room temperatures, of polyethylene terephthalate at various percents of crystallinity as measured by differential scanning calorimetry.

FIG. 2 shows the hydrolysis times, at reflux temperature, of polyethylene terephthalate at various percents of crystallinity using a conventional hydrolysis solution.

DETAILED DESCRIPTION OF THE INVENTION

We have surprisingly found that substantially amorphous polyesters are rapidly converted to their monomeric components by contacting them with a mixture of (a) at least one alcohol, such as methanol, or glycol, (b) at least one polar aprotic solvent such as N-methylpyrrolidone or dimethyl sulfoxide, and (c) at least one alkoxide or hydroxide wherein the alcohol or glycol is capable of dissolving the alkoxide or hydroxide and this solution is in turn soluble in the polar aprotic solvent.

The process of the present invention is particularly useful for the depolymerization or conversion to monomeric components of substantially amorphous polyesters, including copolymers, mixtures thereof and blends of these with other polymers. Highly crystallized polyesters are the most difficult polyesters to depolymerize. However, the process of the present invention depolymerizes these polyesters quite rapidly by converting them to substantially amorphous polyesters by melting and quenching.

We have discovered that the mixture of reagents according to the present processes will hydrolyze substantially amorphous polyesters at extraordinary rates. At crystallinities below about 25 %, the rate is especially fast. Thus the present invention preferably entails the hydrolysis of substantially amorphous polyesters by the process comprising contacting a polyester having a crystallinity percent of no more than about 25% with a compatible mixture of (a) at least one alcohol, (b) at least one polar aprotic solvent, and (c) at least one alkoxide or hydroxide.

According to the process of the present invention, the hydrolysis of polyesters having this low of a crystallinity proceeds rapidly and quantitatively when stirred at atmospheric pressure and ambient temperature. The hydrolysis of amorphous polyesters according to the present invention can easily be completed in less than 60 minutes at ambient conditions with pellets with dimensions between 2 and 3 mm and much faster at elevated temperatures and/or at reduced particle sizes.

Polyesters can be made amorphous by melting followed by rapid cooling. A practical way to accomplish this is by passing the material through an extruder and quenching the molten polymer in some liquid. The quench liquid could be the hydrolysis reagent mixture or one of its components. In this way, the heat from the molten polymer could be used to warm the hydrolysis reagent mixture and speed the reaction.

A preferred process of the present invention comprises:

I) heating a crystalline polyester to form a melt,

II) quenching said melt to form a substantially amorphous polyester, and

III) contacting said substantially amorphous polyester with a mixture of (a) about 5 to 80 (vol) % methanol, (b) about 95 to 20 (vol) % of a polar aprotic solvent selected from the group consisting of dimethyl sulfoxide and N-methylpyrrolidone, and (c) an alkali metal hydroxide in molar excess, with respect to the ester bonds to be hydrolyzed, at a temperature between about room temperature and reflux conditions for a sufficient time to convert said substantially amorphous polyester to its monomeric components.

We have unexpectedly discovered that polyesters, such as polyethylene terephthalate, have dramatically improved hydrolysis times when the crystallinity of the polyester is not much higher than about 25%. As shown in FIG. 1 polyethylene terephthalate is rapidly hydrolyzed at crystallinities below 30%, even at ambient conditions. The dramatic reduction in hydrolysis time commences at low crystallinities of about 27 or 26%. At crystallinity percents below this, the hydrolysis rate is essentially as fast as for fully amorphous material.

Although we believe that the present invention is useful for the depolymerization of any substantially amorphous polyester, examples of suitable polyesters that can be depolymerized by the process of the present invention include: polyethylene terephthalate; polyethylene 2,6-dinaphthalate; and polymers that are prepared from one or more of the following monomers, or esters of these monomers; succinic acid, sebacic acid, azelaic acid, adipic acid, dimer acid, glutaric acid, trans-1,4-cyclohexanedicarboxylic acid, cis,trans-1,4-cyclohexanedicarboxylic acid, 1,3-cyclohexanedicarboxylic acid, isosebacic acid, carbonic acid, pimelic acid, dimethylmalonic acid, suberic acid, 1,12-dodecanedioic acid, terephthalic acid, isophthalic acid, p,p'-methylenedibenzoic acid, 2,6-naphthalenedicarboxylic acid, phthalic acid, dimethyl5-[4-(sodiosulfo)-phenoxy]isophthalate, dimethyl 5-(sodiosulfo)isophthalate, 4,4'-sulfonyldibenzoic acid, 2-(sodiosulfo)-9,9-fluorenebis[propionic acid], 5-[4-(sodiosulfo)-phenoxy]isophthalic acid, 5-[(sodiosulfo)propoxy]-isophthalic acid, trimellitic acid, 4,4'-stilbene dicarboxylic acid, resorcinol bis acetic acid, 4,4'-biphenyl dicarboxylic acid, ethylene glycol, 1,3-trimethylene glycol, 1,4-butanediol, 1,5-pentanediol, 1,6-hexanediol, 2,2-dimethyl-1,3-propanediol, 1,4-cyclohexanedimethanol, bisphenol A, 2,2,4,4-tetramethyl-1,3-cyclobutanediol, 4,4'-(2-norbornylidene)diphenol, 4,4'-(Hexahydro-4,7-methanoindan-5-ylidene)diphenol, 4,4'-[(3-methyl-2-norbornyl)methylene]diphenol, 4,4'-(2-Norbornylidene)bis(2,6-dichlorophenol), 4,4'-(2-norbornylmethylene)diphenol, 5,6,7,8,-tetrahydro-1,4-naphthalenediol, hydroquinone, t-butyl hydroquinone, diethylene glycol, glycerin, trimethylol propane, trimethylol ethane, poly(tetramethylene glycol), poly(propylene glycol), tischenko glycol, 2,2'-[isopropylidene(p-phenyleneoxy)]diethanol, poly(ethylene glycol)(carbowax) (any molecular weight), poly(oxyethylene oxypropylene) (pluronics) (any molecular weight),4-(hydroxymethyl)cyclohexanecarboxylic acid, hydroxypivalic acid, 6-hydroxyhexanoic acid, and p-hydroxybenzoic acid. The most preferred polymer, however, due to its wide spread use and emphasis on its recycle is polyethylene terephthalate.

The process of the present invention is useful in the analysis of the monomer content of these polyesters; the recovery of monomers from polyester scrap such as bottles, trays, fibers, etc.; and the removal of polyester from coated substrates such as dirty polyester processing equipment. The process of the present invention is useful for the depolymerization of substantially amorphous polyesters in whatever form, and crystalline polyesters that can be rendered substantially amorphous. Though the grinding step is not necessary, smaller polyester particles have a larger surface area and are much more rapidly converted to the monomers. Therefore, the particulate form of polyester is more preferred.

The process of the present invention can be conducted at room temperature under mild conditions. However, increased temperature as with increased agitation does reduce conversion time. The upper temperature limit is determined by the capability of the equipment and stability of the products and should not be so high as to decompose the products. The process of the present invention is preferably conducted at a temperature between about room temperature and 200° C., with a temperature at or near room temperature being most preferred. The upper limit of the temperature of the conversion process is dependent upon the reactant materials when the conversion is conducted at refluxing conditions because the temperature is limited by the boiling temperature of the mixture. We have found that as the molecular weight of the alcohol or glycol increases the reflux temperature increases, however, the solubility of the alkoxide or hydroxide in the final solution decreases which tends to reduce the rate of reaction.

The process of the present invention is preferably conducted at atmospheric pressure. However, elevated pressures increase the boiling or refluxing point of the mixture thereby allowing the temperature to rise near the upper range and increasing the rate of conversion. However, the rate of conversion in the process of the present invention is so fast that elevated temperatures near the boiling point of the mixture are not needed thus elevated pressures are not required and not preferred.

The alcohol or glycol used in the present invention can be any alcohol or glycol that is capable of dissolving the hydroxide or alkoxide. However, the preferred alcohols are $C_1$ to $C_4$ alcohols with methanol being the most preferred and the preferred glycol is ethylene glycol.

Any polar aprotic solvent is useful in the present invention so long as the base (alkoxide or hydroxide) in combination with the alcohol or glycol can be dissolved therein. Examples of suitable polar aprotic solvents include dimethyl formamide, dimethyl sulfoxide, sulfolane, hexamethylphosphoramide, and N-methylpyrrolidone. Dimethyl sulfoxide and N-methylpyrrolidone are most preferred due to their cost, availability, purity, toxicity, and rate of reaction.

The alkoxides or hydroxides useful in the present invention are those that are substantially soluble in the final solution. The preferred alkoxides are $C_1$ to $C_4$ alkoxides. The preferred hydroxides are selected from the group consisting of alkali metal hydroxides, alkaline-earth metal hydroxides, tetra-alkyl ammonium hydroxides, and ammonium hydroxide. In the process of the present invention, the hydroxides are preferred over sodium hydroxide, potassium hydroxide and tetra-alkyl ammonium hydroxide.

For each mole of monomeric diacid unit in the polymer two moles of alkoxide or hydroxide are required for a complete conversion to occur since the acid generally has two ester bonds. However, since the rate of reaction is proportional to the concentration of alkoxide or hydroxide in solution, it is preferred that the alkoxide or hydroxide be in substantial molar excess with respect to the ester bonds in the polymer so that complete conversion of the polymer to the monomers can occur rapidly. The molar ratio of alkoxide or hydroxide to the ester bonds in the polymer is preferably greater than 1/1 with greater than 1.5/1 being more preferred. The upper limit of this molar excess is limited by the solubility of the alkoxide or hydroxide in the mixture. However, an amount in excess of this can be present as solid in the mixture to enter solution as alkoxide or hydroxide is depleted.

We have found that the alcohol or glycol functions to enhance the solubility of the alkoxide or hydroxide in the polar aprotic solvent. Its concentration in the mixture should be high enough to dissolve sufficient hydroxide or alkoxide so that the reaction proceeds at a rapid rate. However, excess alcohol or glycol is detrimental because it dilutes the beneficial effect of the polar aprotic solvent.

We have found that the presence of the polar aprotic solvent enhances the rate of reaction above that which can be achieved by the mixture of alcohol or glycol and alkoxide or hydroxide alone. Hence, a high concentration of polar aprotic solvent is desirable. However, hydroxides and alkoxides are generally not as soluble in polar aprotic solvents as they are in alcohols and glycols. If the concentration of polar aprotic solvent becomes too large the concentration of hydroxide or alkoxide in solution will decrease to the point where the beneficial effects of increasing the concentration of the polar aprotic solvent will be cancelled by a decrease in hydroxide or alkoxide concentration.

In light of what we have discovered the preferred ratio of polar aprotic solvent to alcohol or glycol will vary depending upon which polar aprotic solvent, alcohol or glycol, or hydroxide or alkoxide is used. In each case, the fastest reaction rates will be determined by a compromise between increasing the hydroxide or alkoxide solubility by the alcohol or glycol and enhancing the rate by maximizing the concentration of the polar aprotic solvent.

For example, when the components are as follows: dimethyl sulfoxide or N-methylpyrrolidone as the polar aprotic solvent; sodium or potassium hydroxide as the alkoxide or hydroxide; and methanol as the alcohol or glycol, the preferred amounts of components are as follows: between about 10 and 99 volume % polar aprotic solvent; between about 0.5 molar and a saturated solution of hydroxide; and between about 90 and 1 volume methanol. The more preferred amounts of these are 20 and 95 volume % dimethylsulfoxide or N-methylpyrrolidone and 80 and 5 volume % methanol, saturated with hydroxide.

In some instances complete conversion of all polymer may not be desirable. If this is desired, the polymer is simply removed from contact with the solution when sufficient depolymerization has occurred.

The sequential addition of the components of the mixture or solution used in the process of the present invention is not critical. However, it is preferred that the alkoxide or hydroxide be dissolved in the alcohol or glycol prior to the addition of the polar aprotic solvent which is then followed by the addition of the polymer.

The container or reactor used in conducting the process of the present invention is not critical; however, it is preferred that the process of the present invention be conducted in a container in the presence of agitation such as a stirred batch reactor or a continuous reactor. Though not critical the use of a continuous reactor is the more preferred method of employing the process of the present invention. Conducting the process of the present invention in a continuous process is a major advantage over high pressure reactors which must be conducted batch wise.

At the completion of the reaction (conversion) the acid monomers are usually in the form of salts of the acids and are usually insoluble in the reaction mixture. These insoluble salts can be recovered by any conventional process such as by filtration. The recovered monomer salts can be converted back to their acid form by the addition of acid. Alternatively, if it is desired the acid monomer can be separated from the solution by the addition of acid to precipitate the acids followed by filtration recovery.

The process of the present invention is preferably conducted in the absence of water. Anhydrous conditions are preferred since the rate of conversion decreases as the amount of water increases.

The major advantage of the process of the present invention over conventional processes is the increased rate of conversion at relatively mild conditions of pressure and temperature.

The following examples are presented to illustrate the present invention but are not intended to limit the reasonable scope thereof. reasonable scope thereof.

EXAMPLES

The following examples show the unexpected rapid rate of hydrolysis of at least partially amorphous polyester at room temperature.

EXAMPLE 1

One mL of 5 molar sodium hydroxide in methanol was added to four mL of dimethyl sulfoxide. A 0.25 gram sample of amorphous polyethylene terephthalate pellets (less than 1% crystallinty determined by differential scanning calorimetry), approximately 2 mm×2 mm×3 mm, was added to the solution and the mixture was stirred at room temperature. The experiment was repeated 12 times with an average hydrolysis time of 55 min and a range of from 38 to 66 min. There is some variability in the times between experiments because there is some variability in pellet size and this has an effect on hydrolysis time.

EXAMPLE 2

The above Example 1 was repeated three times, also at room temperature, with n-methylpyrrolidone instead of dimethyl sulfoxide. Hydrolysis times were 140, 163, and 165 minutes.

EXAMPLE 3

Examples 1 and 2 were repeated at reflux temperature (about 120° C.) it took only 2 minutes to hydrolyze the amorphous pellets in dimethyl sulfoxide or n-methylpyrrolidone.

EXAMPLE 4

Examples 1 and 2 were repeated with highly complete hydrolysis in dimethyl sulfoxide or n-methylpyrrolidone at room temperature. At reflux temperature (about 120° C.) highly crystallized pellets (37% crystallinity) hydrolyzed after 5 minutes and 7 minutes in dimethyl sulfoxide and n-methylpyrrolidone, respectively.

EXAMPLE 5

This example demonstrates how highly crystallized polyester can be made amorphous by melting and quenching, and thereby increase hydrolysis rate. Crystallized polyethylene terephthalate (37% crystallinity) was melted at 271° C. in a Tinius-Olsen testing machine. The melted polymer was extruded into a 1 mm rod and quenched in water. After quenching, the polymer was blotted with paper towels to remove excess water and allowed to dry at room temperature for 2 hours. A 0.25 gram sample of quenched polymer (7% crystallinity), approximately 1 mm×6 mm lengths, was added to 1 mL of 5 molar sodium hydroxide in methanol and 4 mL of dimethyl sulfoxide. The mixture was stirred at room temperature. After 47 minutes the polymer hydrolyzed.

EXAMPLE 6

Example 5 was repeated except that the melted polymer was quenched in dimethyl sulfoxide. After quenching, the polymer was rinsed with methanol and blotted dry with paper towels. A 0.25 gram sample, approximately 1 mm×6 mm lengths, was added to 1 mL of 5 molar sodium hydroxide in methanol and 4 mL of dimethyl sulfoxide. The mixture was stirred at room temperature. After 26 minutes the polymer hydrolyzed.

EXAMPLE 7

Example 6 was repeated except the melted polymer was quenched in the hydrolysis reagent (20/80 5 molar sodium hydroxide in methanol/dimethyl sulfoxide). The polymer hydrolyzed after 26 minutes at room temperature.

The above Examples 1–7 show the dramatic increase in hydrolysis rate between highly crystallized and essentially amorphous polyester.

The following Examples 8, 9 and 10 show the hydrolysis rate of polyester of various crystallinities at room temperature. These data are compared in FIG. 1.

EXAMPLE 8

In this example amorphous polyethylene terephthalate pellets, approximately 2 mm×2 mm×3 mm, were crystallized for 5 minutes at temperatures ranging from 95° C. to 155° C. in 5° C. increments. This produced crystallinities ranging from 3% to 32%. Crystallinity was measured by differential scanning calorimetry. A 0.25 gram sample of these pellets from each of these crystallization times was added to 5 molar sodium hydroxide in methanol and 4 mL of dimethyl sulfoxide. The mixture was stirred at room temperature. Hydrolysis times from 44 to 320 min were observed. See FIG. 1.

EXAMPLE 9

Amorphous polyethylene terephthalate pellets, approximately 2 mm×2mm×3 mm, were also crystallized at 120° C. for 5, 7, 10, 15, 20, 25 and 30 minutes. This was also repeated at 122° C. instead of 120° C. for 5 and 10 minutes. These experiments produced crystallinities ranging from 10% to 30%. Crystallinity was measured by differential scanning calorimetry. A 0.25 gram sample of these pellets from each of these crystallization times was added to 1 mL of 5 molar sodium hydroxide in methanol and 4 mL of dimethyl sulfoxide. The mixture was stirred at room temperature. Hydrolysis times from 53 to 660 min were observed. See FIG. 1.

EXAMPLE 10

Amorphous polyethylene terephthalate pellets, approximately 2 mm×2 mm×3 mm, were also crystallized at 120° C. for 5, 6, 7, 8, 9 and 10 minutes. This produced crystallinities ranging from 12% to 31%. Crystallinity was measured by differential scanning calorimetry. A 0.25 gram sample of these pellets from each of these crystallization times was added to 1 mL of 5 molar sodium hydroxide in methanol and 4 mL of dimethyl sulfoxide. The mixture was stirred at room temperature. Hydrolysis times of 59 to 390 min were observed. See FIG. 1.

EXAMPLE 11

This example shows the hydrolysis times of at least partially amorphous polyester at increased temperatures using conventional hydrolysis mixtures. Amorphous polyethylene terephthalate pellets, amorphous pellets crystallized at 120° C. for 5, 6, 7, 8, and 9 minutes, and amorphous pellets crystallized at 180° C. for 30 minutes were used. These pellets had crystallinities ranging from 1% to 38%. Crystallinity was measured by differential scanning calorimetry. A 0.25 gram sample of these pellets from each of these crystallization times, approximately 2 mm×2 mm×3 mm, was added to 5 mL of 1 molar potassium hydroxide in n-propanol. The of 1 molar potassium hydroxide in n-propanol. The mixture was stirred at reflux, about 110° C. Hydrolysis times of 7 to 39 minutes were observed. See Table 1 and FIG. 2.

EXAMPLE 12

This example was performed using the same pellets as described in Example 11. A 0.25 gram sample of these pellets from each crystallization time was added to 1 mL of 5 molar sodium hydroxide in methanol and 4 mL dimethyl sulfoxide. The mixture was heated at 40° C. Hydrolysis times of 17 to 98 minutes were observed. This experiment was then repeated at 50° C. instead of 40° C. Hydrolysis times of 21 to 51 minutes were observed. Again this experiment was repeated at 80° C. instead of 40° C. Hydrolysis times of 2 to 10 minutes were observed. See Table 1.

TABLE 1

| | Hydrolysis Times at Various Crystallinities and Temperatures | | | |
|---|---|---|---|---|
| Percent Crystallinity | Hydrolysis Times* at 40° C. in minutes | Hydrolysis Times* at 50° C. in minutes | Hydrolysis Times* at 80° C. in minutes | Hydrolysis Times** at 110° C. in minutes |
| 1% | 17,23 | 21 | 2 | 7 |
| 12% | 40,45,51 | 28 | 3 | 10 |
| 13% | 25,31,39 | 26 | 4 | 9 |
| 26% | 32,36 | 24 | 5 | 11 |
| 27% | 66,67 | 41 | 7 | 19 |
| 31% | 85,87 | 48 | 8 | 22 |
| 38% | 94,98 | 51 | 10 | 39 |

*DMSO Hydrolysis Reagent
**Conventional Hydrolysis Reagent

EXAMPLE 13

This example illustrates the hydrolysis of polyethylene terephthalate in a form other than pellets. An experiment was performed using the sidewall of a commercial polyethylene terephthalate beverage bottle (33% crystallinity). A 0.25 gram sample of bottle sidewall, approximately 3 mm×3 mm×1 mm, was added to 1 mL of 5 molar sodium hydroxide in methanol and 4 mL of dimethyl sulfoxide. The mixture was stirred at room temperature. After 80 minutes the polymer hydrolyzed.

EXAMPLE 14

This example was performed using a different polyester, amorphous polyethylene naphthalate pellets. A 0.25 gram sample of pellets, approximately 1 mm×2 mm×3 mm, was added to 1 mL of 5 molar sodium hydroxide in methanol and 4 mL of dimethyl sulfoxide. The mixture was stirred at room temperature. After 10 hours the pellets hydrolyzed. This experiment was repeated with crystallized (37% crystallinity) instead of amorphous pellets. After 24 hours the pellets hydrolyzed. These experiments were repeated with approximately 4 mm×4 mm cylindrical pellets instead of 1 mm×2 mm×3 mm pellets. After 15 hours and 40 hours the amorphous and crystallized (44% crystallinity) pellets hydrolyzed, respectively. These experiments were repeated but the mixtures were heated at reflux. At reflux temperature, about 120° C., it took 4 minutes to hydrolyze the 1 mm×2 mm×3 mm and the 4 mm×4 mm amorphous pellets. At reflux temperature it took 7 and 12 minutes to hydrolyze the 1 mm×2 mm×3 mm and the 4 mm×4 mm crystallized pellets, respectively.

What is claimed is:

1. A process for the conversion of polyesters to their monomeric components comprising contacting a substantially amorphous polyethylene terephthalate having a crystallinity of no greater than 25% with a mixture of (a) at least one alcohol or glycol; (b) at least one polar aprotic solvent; and (c) at least one alkoxide or hydroxide for a sufficient time to convert at least a portion of said polyester to it's monomeric components; wherein said alcohol or glycol, said polar aprotic solvent, and said alkoxide or hydroxide are compatible, bringing at least a portion of said alkoxide or hydroxide into solution in the solvent mixture.

2. The process according to claim 1 wherein the amount of component (a) is between about 5 and 80 volume % and the amount of component (b) is between about 95 and 20 volume %.

3. The process according to claim 2 wherein component (c) is in a concentration between 0.5 molar and saturated condition in the solvent mixture of components (a) and (b).

4. The process according to claim 1 wherein said substantially amorphous polyethylene terephthalate i in particulate form.

5. The process according to claim 1 wherein said alcohol is selected from the group consisting of C1 to C4 alcohols; said glycol is ethylene glycol; said polar aprotic solvent is selected from dimethyl formamide, dimethyl sulfoxide, sulfolane, hexamethyl-phosphoramide, and N-methylpyrrolidone; said alkoxide is elected from the group consisting of $C_1$ to $C_4$ alkoxides; and said hydroxide is selected from the group consisting of alkali metal hydroxides, alkaline-earth metal hydroxides, tetra-alkyl ammonium hydroxide, and ammonium hydroxide.

6. The process according to claim 1 wherein said alcohol or glycol is selected from the group consisting of $C_1$ to $C_4$ alcohols.

7. The process according to claim 6 wherein said alcohol or glycol is methanol; said polar aprotic solvent is selected from dimethyl sulfoxide and N-methylpyrrolidone; and said alkoxide or hydroxide is selected from the group consisting of sodium hydroxide, potassium hydroxide or tetra alkyl ammonium hydroxide.

8. The process according to claim 1 wherein said substantially amorphous polyethylene terephthalate is contacted with said mixture at a temperature between about room temperature and about 200° C.

9. The process according to claim 8 wherein said substantially amorphous polyethylene terephthalate is contacted with said mixture at about room temperature.

10. The process according to claim 1 wherein said mixture is in substantially anhydrous conditions.

11. The process according to claim 1 wherein said alkoxide or hydroxide is dissolved in said alcohol or glycol prior to the addition of said polar aprotic solvent.

12. The process according to claim 1 wherein said alkoxide or hydroxide is present in a molar excess with respect to ester bonds in said substantially amorphous polyethylene terephthalate.

13. The process according to claim 1 further comprising, prior to said contacting, heating a crystalline polyethylene terephthalate to form a melt and quenching said melt into a liquid to form a substantially amorphous polyethylene terephthalate.

14. The process according to claim 13 wherein said liquid is at least one component of said mixture of (a), (b) and (c).

15. A process for the conversion of polyesters to their monomeric components comprising:
   I) heating a crystalline polyethylene terephthalate to form a melt,
   II) quenching said melt to form a substantially amorphous polyethylene terephthalate having a crystaliniity no greater than 25%, and
   III) contacting sad substantially amorphous polyethylene terephthalate with a mixture of (a) about 5 to 80 (vol) % methanol, (b) about 95 to 20 (vol) % of a polar aprotic solvent selected from the group consisting of dimethyl sulfoxide and N-methyl-pyrrolidone, and (c) an alkali metal hydroxide in molar excess, with respect to the ester bonds to be hydrolyzed, at a temperature between about room temperature and the boiling point of the mixture for a sufficient time to convert said substantially amorphous polyethylene terephthalate to its monomeric components.

16. A process for the conversion of polyesters to their monomeric components comprising:
   A) heating crystalline polyethylene terephthalate to form a melt, and
   B) quenching said melt into a liquid to form a substantially amorphous polyethylene terephthalate having a crystallinity no greater than 25%, wherein said substantially amorphous polyethylene terephthalate is contacted with a mixture of (a) about 5 to 80 (vol) % methanol, (b) about 95 to 20 (vol) % of a polar aprotic solvent selected from the group consisting of dimethyl sulfoxide and N-methyl-pyrrolidone, and (c) an alkali metal hydroxide in molar excess, with respect to the ester bonds to be hydrolyzed, in said polyethylene terephthalate and said liquid is at least one component of the mixture of (a), (b) and (c).

* * * * *

UNITED STATES PATENT AND TRADEMARK OFFICE
CERTIFICATE OF CORRECTION

PATENT NO. : 5,328,982
DATED : July 12, 1994
INVENTOR(S) : G. W. Tindall, R. L. Perry, A. T. Spaugh, Jr.

It is certified that error appears in the above-indentified patent and that said Letters Patent is hereby corrected as shown below:

Column 9, line 52 after terephthalate remove "i" and insert - - - is - - -.

Column 10, line 37 remove "talinnty" and insert - - - tallinity - - -.

Signed and Sealed this

Eighth Day of November, 1994

Attest:

BRUCE LEHMAN

Attesting Officer                Commissioner of Patents and Trademarks